(12) United States Patent
Zell

(10) Patent No.: US 7,393,112 B1
(45) Date of Patent: Jul. 1, 2008

(54) WINE ILLUMINATOR

(75) Inventor: Jeffrey M. Zell, Potomac, MD (US)

(73) Assignee: JM Zell Partners, Ltd., Washington, DC (US)

( * ) Notice: Subject to any disclaimer, the term of this patent is extended or adjusted under 35 U.S.C. 154(b) by 71 days.

(21) Appl. No.: 11/614,567

(22) Filed: Dec. 21, 2006

(51) Int. Cl.
*F21V 33/00* (2006.01)
(52) U.S. Cl. .......................................... 362/101; 362/96
(58) Field of Classification Search ................... 362/96, 362/101, 154, 802; 215/399
See application file for complete search history.

(56) References Cited

U.S. PATENT DOCUMENTS

| | | | |
|---|---|---|---|
| 1,249,341 A | 12/1917 | Cropsey | |
| 2,177,337 A | 10/1939 | Stein | 240/6.4 |
| 2,547,450 A | 4/1951 | Du Pont | 222/113 |
| 2,596,452 A | 5/1952 | Wehmiller et al. | 88/14 |
| 3,868,047 A | 2/1975 | Bersano | 222/166 |
| 4,344,113 A | 8/1982 | Ditto et al. | 362/101 |
| 4,496,124 A | 1/1985 | Cole | 248/146 |
| 4,515,334 A | 5/1985 | Horne | 248/146 |
| 4,836,476 A | 6/1989 | Wolf | 248/146 |
| 5,026,480 A | 6/1991 | Fischer | 210/515 |
| D329,781 S | 9/1992 | Ito | D7/619 |
| 5,307,250 A | 4/1994 | Pearson | 362/101 |
| 6,174,066 B1 | 1/2001 | Vinding-Diers | 362/96 |
| 6,254,247 B1 | 7/2001 | Carson | 362/101 |
| 6,425,421 B1 | 7/2002 | Morrison | 141/64 |
| 6,793,363 B2 | 9/2004 | Jensen | 362/101 |
| 2002/0108672 A1 | 8/2002 | Morrison | 141/64 |
| 2004/0035296 A1 | 2/2004 | Schauz et al. | 99/275 |
| 2005/0191395 A1 | 9/2005 | Creasey et al. | 426/335 |

FOREIGN PATENT DOCUMENTS

FR 2805724 A1 * 9/2001

* cited by examiner

*Primary Examiner*—Hargobind S Sawhney
(74) *Attorney, Agent, or Firm*—Paul F. McQuade; Greenberg Traurig, LLP

(57) ABSTRACT

An apparatus for illuminating wine or other liquids, whereby the user can limit the amount of sediment that is allowed to escape from the bottle. The apparatus comprises a collar, an arm, a body, a light source, and a switch. The collar can be hingedly attached to the arm with a spring-loaded hinge. The collar can have a hole large enough to accommodate the neck of a majority of wine or other bottles currently manufactured. The body can be attached to the arm via a retaining member, such that the body is freely positionable along the arm. The light source can be fixedly attached to the body, or hingedly attached thereto.

22 Claims, 5 Drawing Sheets

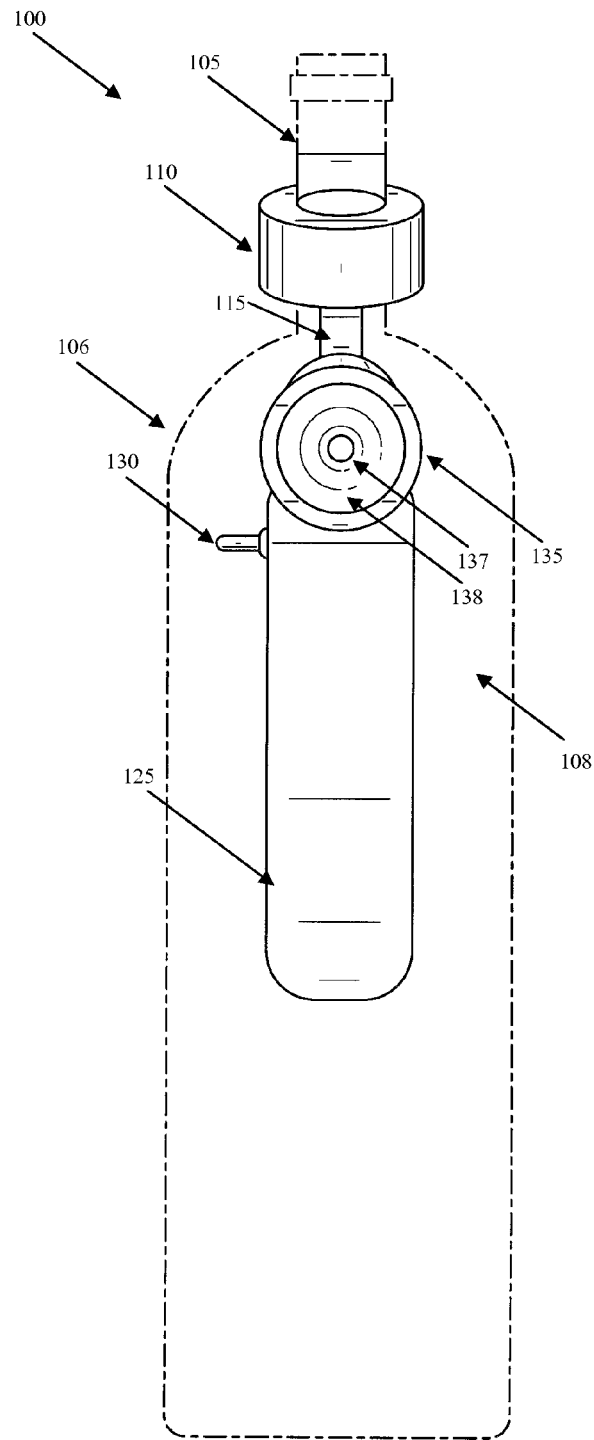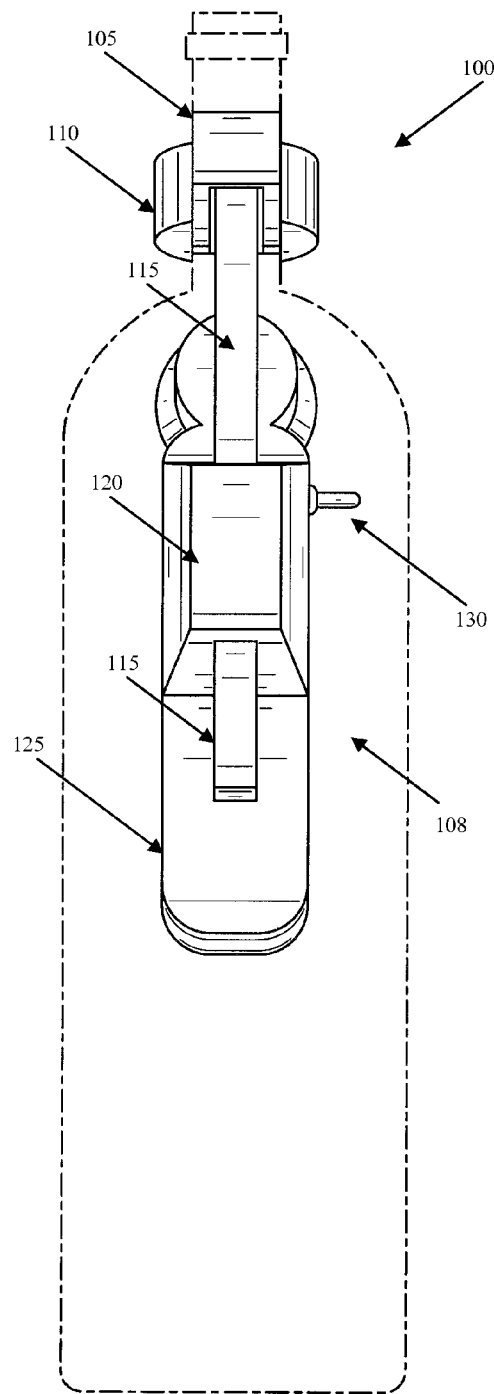
FIGURE 2  FIGURE 3

WINE ILLUMINATOR

FIELD

The instant disclosure relates to the field of decanting wine in general and, in particular, to an illuminating apparatus and method that is used to ensure that sediments suspended in the wine are retained in the bottle and do not flow into the decanter used to prepare the wine for consumption.

BACKGROUND

Of great to concern to wine connoisseurs is the proper handling and decanting of their wine bottles to ensure that proper taste, aroma and texture are preserved. Typically, during the aging process, wine bottles rest on their sides at a slight angle for months, years, or even decades, during which time sediment settles out of the wine. Standing a bottle during opening causes the sediment to return into suspension, which alters the taste of the wine. As stated by Bob Dickinson in his article "Demolishing a Decanting Myth" (Bob Dickinson, *Demolishing a Decanting Myth*, Wine Spectator, Jul. 31, 2005, at 109), sediment, lees, or particulates (referred to herein collectively as "sediment" for clarity) may make wine "inherently bitter and mask[ ] the flavor of the wine." Some in the prior art have developed techniques and devices for removing sediment prior to consumption of the wine.

One method of reducing the amount of sediment present in a glass of wine is to decant the wine. Decanting involves pouring the wine from its original bottle into another receptacle, typically a decanter. The pouring process is stopped immediately prior to when the sediment present in the original bottle would flow into the receptacle.

While proper decanting can significantly reduce the amount of sediment poured into the receptacle, it is critical that the pouring process be closely monitored. Because the general presumption is to under-pour, rather than risk introducing sediment into the decanter, 10-15% of the fluid volume of the wine is frequently left in the original bottle. While that percentage loss may not seem substantial, it represents a significant financial loss and diminishment of the potential enjoyment that would have been derived from the wine.

As can be seen in U.S. Patent Application Publication No. 20020108672 to Morrison, one prior art approach utilizes pumping and/or pressurized systems to transfer the fluid content of the wine bottle into a receptacle. Morrison uses a complex combination of a siphon, a pump, and a support to draw the wine away from the sediment and into the receptacle unit. While the Morrison system can reduce the amount of sediment introduced into the receptacle, Morrison does not allow the wine pourer to visually inspect and monitor the wine during decanting. Thus, there is still a chance that sediment may be introduced.

Another attempt at reducing the amount of sediment introduced into the receptacle is described in U.S. Patent Application Publication No. 20040035296 to Schaus. The Schaus method utilizes a centrifugal device at the beginning stages of the winemaking process. This centrifugal device separates out the sediment present at that time. However, this process does not account for sediment that develops during aging. This process also does not allow the wine pourer to visually inspect and monitor the wine during decanting.

Still others have attempted to reduce the amount of sediment introduced into the receptacle by illuminating at least a portion of the wine as it is poured from the bottle. Some of these illuminating apparatuses involve complex arrangements of pulleys and hand-operated levers, such as that described in U.S. Pat. No. 3,868,047 to Bersano. Others, such as the decanting apparatus described in U.S. Pat. No. 5,026,480 to Fischer, incorporate the light into a curved carrier into which both the wine bottle and decanter are placed. Still others, such as the illuminating device illustrated in U.S. Pat. No. 6,174,066 to Vinding-Diers, incorporate the light into an apparatus that attaches to the wine bottle at multiple points, and which is also used as a handle.

SUMMARY

While these illuminators may work, each has its own disadvantage. By way of example, without limitation, the Bersano illuminator is likely to be too large and too expensive for all but the most sophisticated buyers. The Fischer illuminator requires a relatively large surface area over which to operate the device. Vinding-Diers has the advantage of being relatively compact, but the design has several other flaws. For example, as described in column 2, lines 36-38, the upper collar is of a fixed diameter, and requires "an energetic push from the top downward" to be installed over a particular size bottle, and the housing has a "back surface 28 with a profile shaped so as to fit against the outer profile of the shoulder 18 and neck 16 of the bottle in generally confronting relation". Because the shape of a wine bottle may vary from bottle manufacturer to bottle manufacturer, and even based on the volume of wine in the bottle, the Vinding-Diers apparatus is suitable for only a single style of bottle. Still further, Vinding-Diers discloses that the apparatus described therein should be used as a handle, with the user's fingers wrapped around the apparatus. However, with the user's hand in such a position, and given the position of the light within the apparatus, the user's hand will obstruct his or her view of the wine as it is being decanted.

As will be appreciated by wine aficionados, a longstanding need has existed among connoisseurs of fine vintage wines for a new and improved wine decanting method and apparatus that allows the wine pourer to remove almost the entire fluid volume of a bottle of wine, and which also provides enhanced sediment detection. The provision of such a method and apparatus is an objective of the disclosed wine illuminator.

Accordingly, the instant disclosure is directed to a method and apparatus for illuminating wine during decanting that substantially obviates one or more of the problems due to limitations and disadvantages of the related art.

Additional features and advantages will be set forth in the description which follows, and in part will be apparent from the description, or may be learned by practice of the disclosed wine illuminator. The objectives and other advantages of the disclosed wine illuminator will be realized and attained by the structure particularly pointed out in the written description and the appended drawings.

It is to be understood that both the foregoing general description and the following detailed description are exemplary and explanatory and are intended to provide further explanation of the disclosed wine illuminator as claimed.

BRIEF DESCRIPTION OF THE DRAWINGS

The accompanying drawings, which are included to provide a further understanding of the disclosed wine illuminator and are incorporated in and constitute a part of this specification, illustrate embodiments of the disclosed wine illuminator and together with the description serve to explain the principles of at least one embodiment of the disclosed wine illuminator.

FIG. 2 is a front elevation view of an exemplary wine illuminator embodiment.

FIG. 3 is a rear elevation view of an exemplary wine illuminator embodiment.

DETAILED DESCRIPTION

Reference will now be made in detail to embodiments of the disclosed wine illuminator, examples of which are illustrated in the accompanying drawings.

Figure 1:
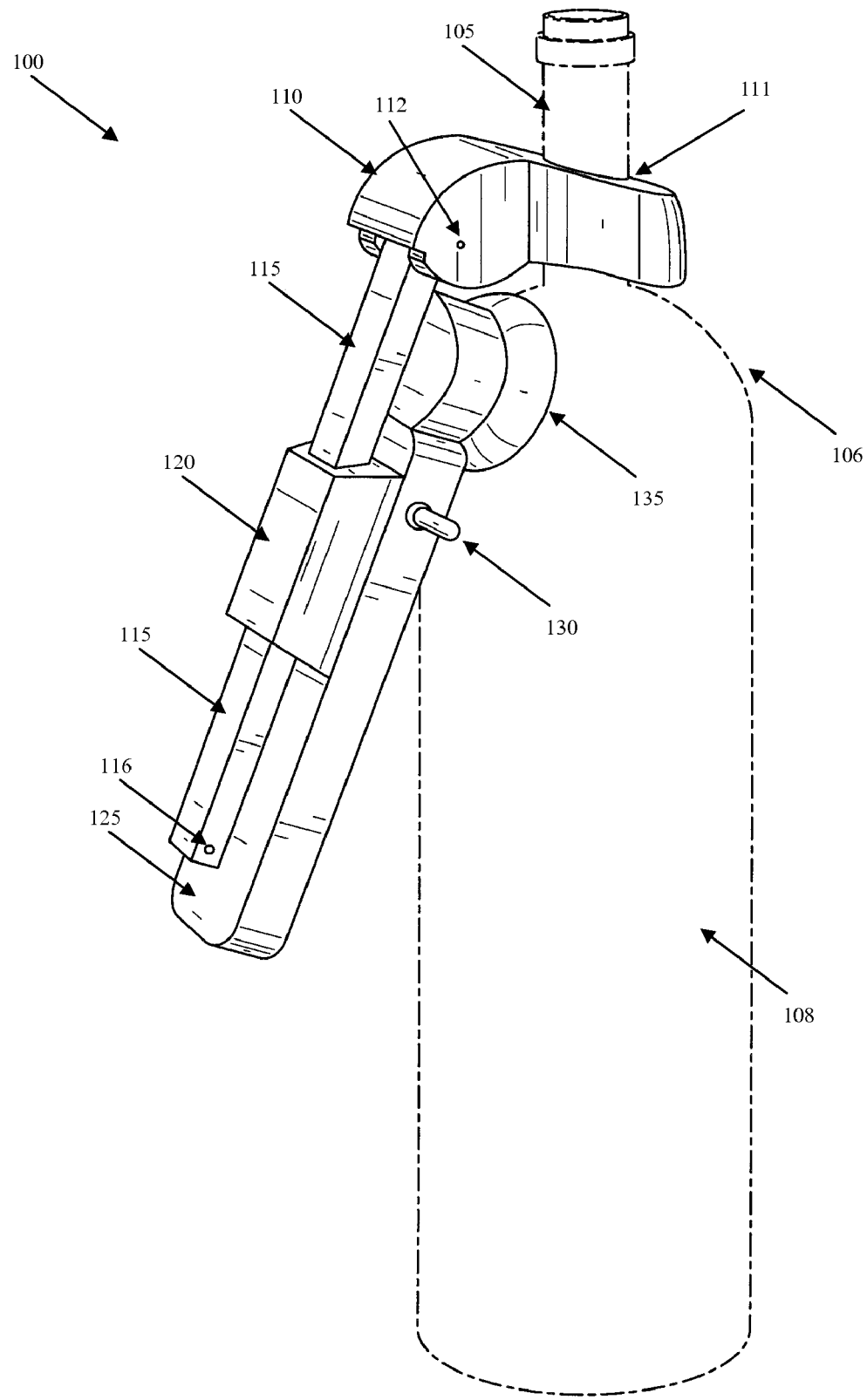
FIG. 1 is a right perspective view of an exemplary wine illuminator embodiment.

FIG. 1 is a right perspective view of an exemplary wine illuminator embodiment 100. As FIG. 1 illustrates, a wine illuminator 100 can comprise a collar 110, arm 115, retaining member 1220, body 125, and light source 135. Collar 110, arm 115, retaining member 120, and body 125 can be made from a variety of materials including, without limitation, wood, plastic, and metal. At least a portion of light source 135 may also be made of such materials.

Collar 110 comprises a hole, wherein the hole is large enough to fit over at least a plurality of bottle neck sizes. When collar 110 is positioned around bottle neck 105, the weight and shape of illuminator 100 can cause the upper edge 111 of collar 110 to engage bottle neck 105 through friction. In an embodiment, the inner surface of collar 110 may comprise a non-skid coating, such as, without limitation, silicone, epoxy, rubber, or the like. An embodiment of collar 110 may comprise one or more rubber O-rings, which also function to limit collar 110's ability to slide on neck 105 when frictionally engaged thereon.

As FIG. 1 further illustrates, illuminator 100 further comprises arm 115. Arm 115 can be hingedly attached to collar 110 via hinge 112. Hinge 112 permits arm 115, and illuminator body 125, to articulate, thereby allowing illuminator 100 to be used with a variety of bottle shapes. In an embodiment, hinge 112 may be spring loaded, such that the collar of light source 135 remains in contact with the hip of bottle 135, even as the contents of bottle 108 are dispensed therefrom.

Figure 7:
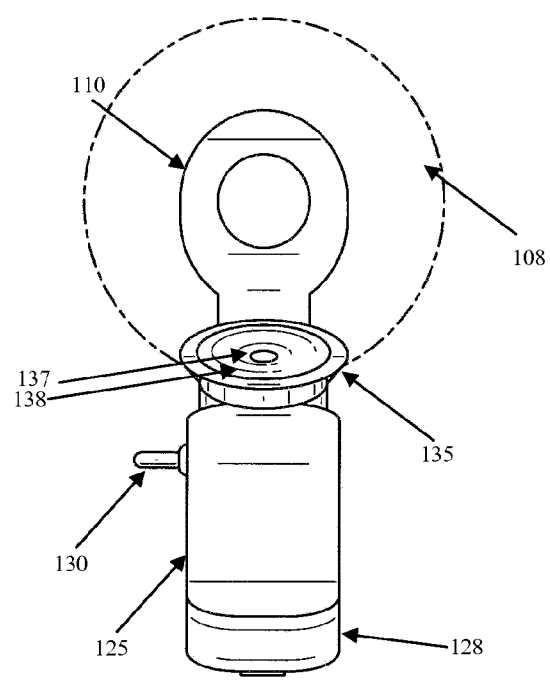
FIG. 7 is a bottom plan view of an exemplary wine illuminator embodiment.

Referring to FIGS. 2 and 7, illuminator 100 may also comprise one or more light sources 135 which are operable via switch 130, which may also control the intensity of the light produced by light sources 135. Light sources 135 may utilize one or more light bulbs 137 to illuminate the contents of bottle 108. Such light bulbs may comprise, without limitation, xenon or other halogen-powered light bulbs, light-emitting diodes, tungsten-powered light bulbs, or the like. In an embodiment, inner surface 138 of light source 135 may comprise a reflective coating, thereby allowing a greater portion of the light produced by bulb 137 to be directed into bottle 108. In an embodiment, light sources 135 are powered by one or more batteries contained within illuminator body 125. Such batteries can be replaced via door 128. In an embodiment, illuminator body 125 may also be capable of receiving power from one or more external power sources, such as, without limitation, power generated by a DC power converter.

Illuminator 100 can be designed such that the light output from light source 135 is aligned substantially perpendicular to bottle 108, thereby providing a light beam that passes through the wine as it is poured. In an embodiment, light source 135 is hingedly attached to illuminator body 125, thereby providing the ability to adjust the angle at which light from light source 135 enters bottle 108. In an embodiment, the surface of light source 135 that rests against bottle 108 may be arranged at an acute angle with respect to illuminator body 125, thereby permitting light source 135 to properly illuminate bottle 108. Such light can enhance the user's ability to detect when sediment is approaching the mouth of bottle 108. Generally, wine will develop a dust-like or smoke-like appearance that informs the wine pourer that the wine might be contaminated by sediment. In the beginning of the pour, there should be little or no sediment in the wine and light from light sources 135 can pass through the wine generating little or no reflectance. As the contents of bottle 108 are poured, the sediment that descended to the base of bottle 108 during storage can move with the contents of bottle 108 toward neck 105. Light from light source 135 can reflect off the sediment and act as warning to the wine pourer of the presence of sediment. Once the wine pourer detects that the shimmers of sediment within the light are substantially approaching neck 105, the wine pourer can halt the decanting or pouring process.

In an embodiment, light source 135 may also comprise a photo detector. The photo detector can take an initial reading of the amount of light passing through the wine, and then monitor the light level as the pour progresses. If the photo detector determines that the light level has degraded beyond a pre-set margin, the photo detector can alert the wine pourer, such as through a visual or auditory stimulus, or cause light level to change depending on the light level reading.

In the embodiment illustrated in FIG. 2, light source 135 comprises a collar which is designed such that hip 105 of bottle 108 can be at least partially received therein. Such a collar may be designed to also work with bottles having a more gradual taper. In an embodiment, the portion of the collar of light source 135 that contacts hip 105 and/or bottle 108 can be coated with a non-skid coating. An embodiment of light source 135 can also comprise one or more o-rings located around the circumference of light source 135's collar. Such o-rings may serve to limit the ability of light source 135 to slide along bottle 108 and/or hip 105.

Figure 6:
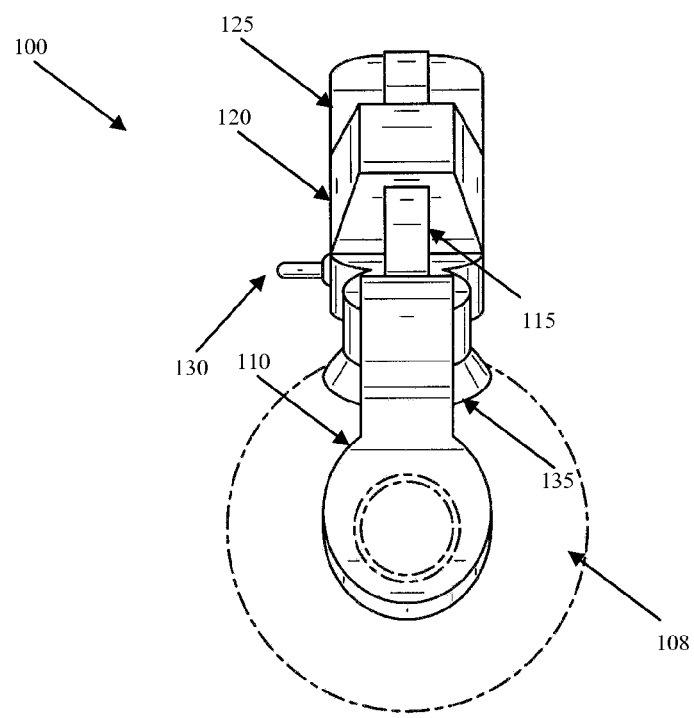
FIG. 6 is a top plan view of an exemplary wine illuminator embodiment.

As FIGS. 3 and 6 illustrate, illuminator 100 comprises retaining member 120, which holds illuminator body 125 to arm 115. In an embodiment, retaining member 120 can be freely positioned along arm 115. In an embodiment, arm 115 may comprise a plurality of detents or the like, and retaining member 120 may comprise one or more members that mate with at least one of the plurality of detents, thereby limiting retaining member 120's ability to move along arm 115 without sufficient external force. In an embodiment, arm 115 may comprise a non-skid coating, which engages retaining member 120 via friction when retaining member 120 is placed at an angle with respect to the plane created by arm 115, such as may occur when illuminator 100 is positioned on bottle 108.

Figure 4:
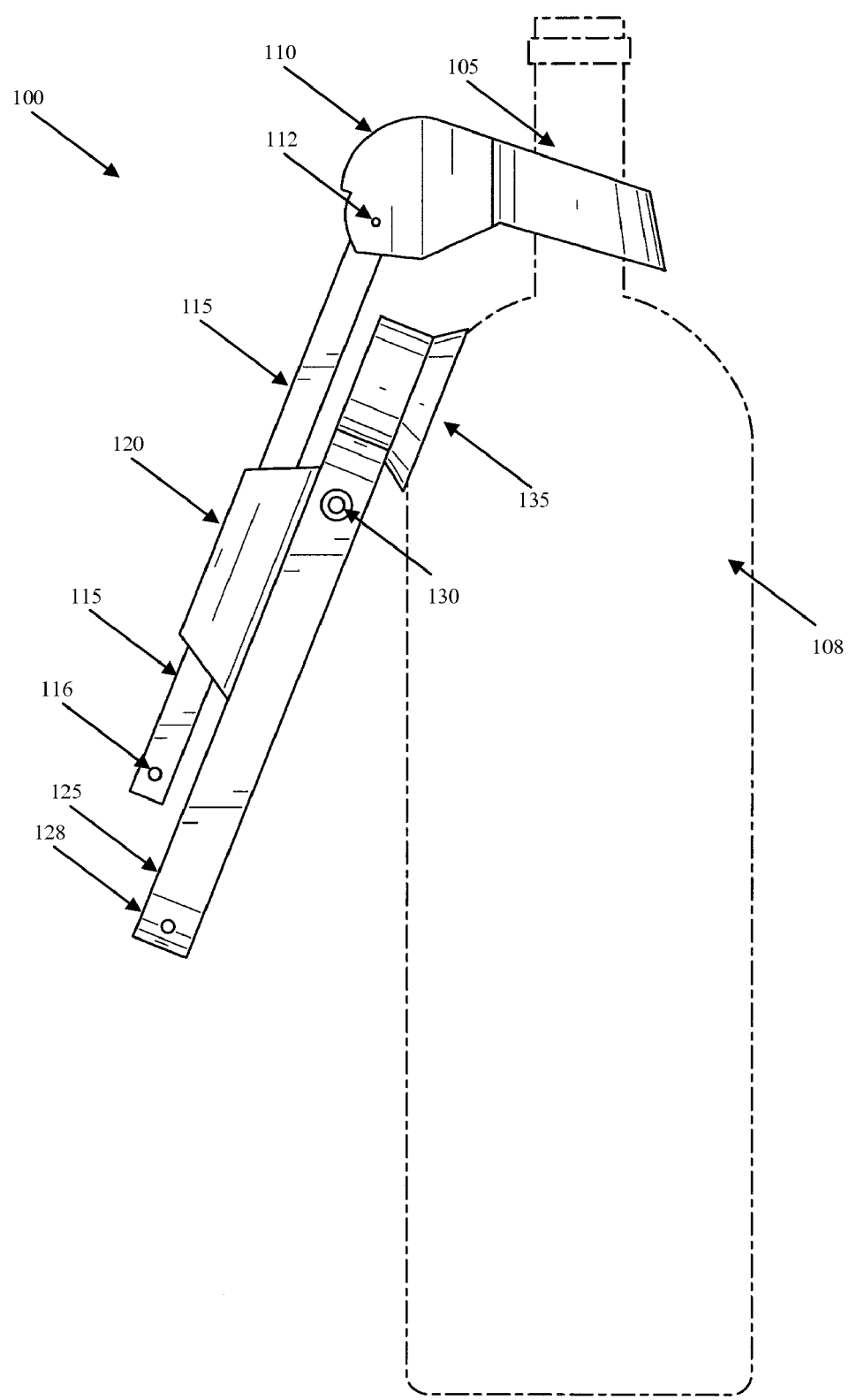
FIG. 4 is a right elevation view of an exemplary wine illuminator embodiment.
Figure 5:
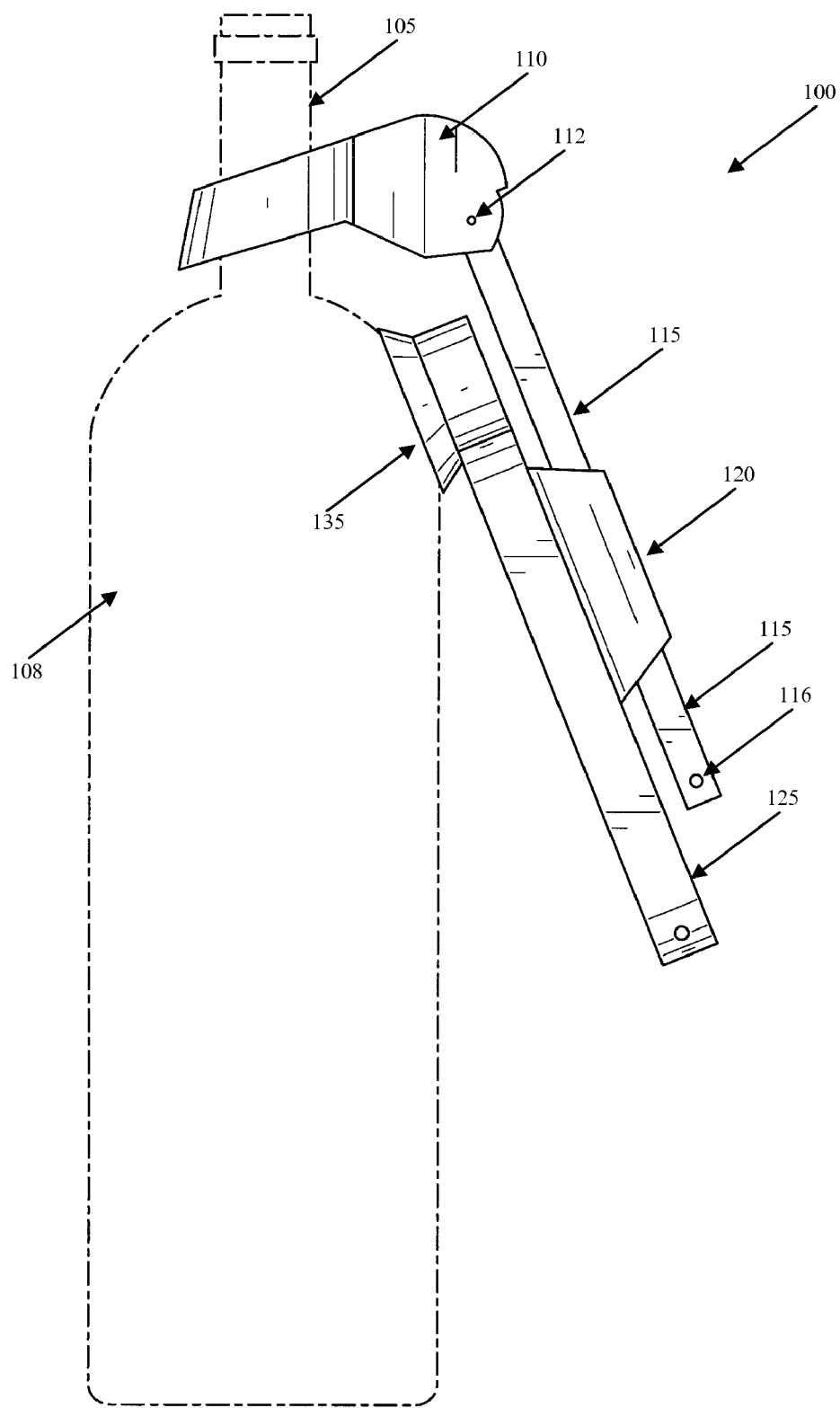
FIG. 5 is a left elevation view of an exemplary wine illuminator embodiment.

As illustrated in FIGS. 4 and 5, Arm 115 (which may telescope or be otherwise adjustable) may also comprise one or more stops 116, which prevent retaining member 120 from coming free from arm 115. In an embodiment, retaining member 116 can be removed from arm 115, temporarily hidden within arm 115, or the otherwise disengaged, thereby permitting illuminator body 125 to be removed from arm 115. Such removal may be advantageous, for example, to aid in cleaning illuminator 100.

While reference has been made herein to specific embodiments and details of a wine illuminator, it will be apparent to those skilled in the art that various changes and modifications can be made therein without departing from the spirit and scope thereof. Thus, it is intended that the instant application cover the modifications and variations of the disclosed wine illuminator, provided they come within the scope of the appended claims and their equivalents.

The invention claimed is:

1. An apparatus for illuminating the contents of a bottle, the bottle comprising a neck, comprising:
   a collar, wherein the collar comprises a hole, and wherein the hole is large enough to permit the neck of the bottle to fit therethrough;
   an arm, wherein the arm is hingedly attached to the collar;
   a body, wherein the body comprises a light source; and,
   a retaining member, wherein the retaining member attaches the body to the arm, and wherein the retaining member permits the body to be moved along at least a portion of the arm.

2. The apparatus of claim 1, wherein hinged connection between the collar and the arm further comprises a spring.

3. The apparatus of claim 2, wherein the spring biases the apparatus such that the body is held proximate to the bottle.

4. The apparatus of claim 1, further comprising a switch, wherein the switch operates the light source.

5. The apparatus of claim 4, wherein the switch controls the intensity of light generated by the light source.

6. The apparatus of claim 1, wherein at least the body comprises wood.

7. The apparatus of claim 1, wherein at least one of the collar, the arm, and the light source further comprises a non-skid material.

8. The apparatus of claim 7, wherein the non-skid material comprises at least one O-ring.

9. The apparatus of claim 7, wherein the non-skid material comprises a rubber coating.

10. The apparatus of claim 9, wherein the rubber coating is silicon.

11. The apparatus of claim 1, wherein the hole has a diameter, and the diameter is selected to be wider than the widest neck of traditional wine bottles.

12. The apparatus of claim 1, wherein the light source comprises at least one light bulb.

13. The apparatus of claim 12, wherein the light source further comprises a reflective surface.

14. The apparatus of claim 1, wherein the light source further comprises a light emitting diode.

15. The apparatus of claim 1, wherein the light source is hingedly connected to the body.

16. The apparatus of claim 1, wherein the arm comprises at least one stop.

17. The apparatus of claim 16, wherein the at least one stop can disengaged.

18. The apparatus of claim 1, wherein a length of the arm is adjustable.

19. The apparatus of claim 18, wherein the arm length is adjusted telescopically.

20. An apparatus for illuminating the contents of a bottle, the bottle comprising a neck, comprising:
    a collar, wherein the collar comprises a hole, and wherein the hole is large enough to permit the neck of the bottle to fit therethrough;
    an arm, wherein the arm is hingedly attached to the collar, the hinge comprising at least one spring, wherein the arm further comprises at least one stop that can be disengaged;
    a body, wherein the body comprises a light source; and,
    a retaining member, wherein the retaining member attaches the body to the arm, and wherein the retaining member permits the body to be moved along at least a portion of the arm.

21. The apparatus of claim 20, wherein at least one of the collar, the arm, and the light source comprise a non-skid material.

22. The apparatus of claim 20, further comprising a switch, wherein the switch controls the operation of the light source.

* * * * *